US008148568B2

(12) United States Patent
Lopp et al.

(10) Patent No.: US 8,148,568 B2
(45) Date of Patent: Apr. 3, 2012

(54) ESTERS OF (2-HYDROXY-3-OXO-CYCLOPENT-1-ENYL) ACETIC ACID AND THEIR USE FOR PREPARING (−)-R-HOMOCITRIC ACID GAMMA-LACTONE, (+)-S-HOMOCITRIC ACID GAMMA-LACTONE AND THE CORRESPONDING (−)-R-HOMOCITRIC ACID AND (+)-S-HOMOCITRIC ACID SALTS

(75) Inventors: Margus Lopp, Tallinn (EE); Anne Paju, Tallinn (EE); Margus Eek, Harjumaa (EE); Marit Laos, Tallinn (EE); Tonis Pehk, Tallinn (EE); Raissa Jaalaid, Tallinn (EE)

(73) Assignees: Tallinn University of Technology, Tallinn (EE); Cambrex Tallinn AS, Tallinn (EE)

( * ) Notice: Subject to any disclaimer, the term of this patent is extended or adjusted under 35 U.S.C. 154(b) by 619 days.

(21) Appl. No.: 12/302,504

(22) PCT Filed: May 25, 2007

(86) PCT No.: PCT/EE2007/000009
§ 371 (c)(1),
(2), (4) Date: Nov. 25, 2008

(87) PCT Pub. No.: WO2007/137593
PCT Pub. Date: Dec. 6, 2007

(65) Prior Publication Data
US 2009/0187041 A1    Jul. 23, 2009

(30) Foreign Application Priority Data

May 25, 2006   (EE) .................................. P200600017

(51) Int. Cl.
*C07C 69/74*   (2006.01)
*C07C 59/245*  (2006.01)
(52) U.S. Cl. ........................................ 560/122; 562/582
(58) Field of Classification Search .................. None
See application file for complete search history.

(56) References Cited

FOREIGN PATENT DOCUMENTS

| EE | 200400009 | 8/2005 |
| JP | 2005075734 | 3/2005 |

OTHER PUBLICATIONS

Paju et al, Tetrahedron, A Short Enantioselective Synthesis of Homocitric Acid-gamma-lactone and 4-Hydroxy-homocitric Acid-gamma-lactones, 1994, 60, pp. 9081-9084.*
Strassman M., Ceci L.N. Enzymic formation of homocitric acid, an intermediate in lysine biosynthesis. Biochemical and Biophysical Research Communications (1964), 14(3), 262-7.
Strassman M., Ceci L.N. Enzymic formation of α-ketoadipic acid from homoisocitric acid. Journal of Biological Chemistry (1965), 240(11), 4357-61.
Hogg R. W., Broquist H. P. Homocitrate formation in *Neurospora crassa*. Relation to lysine biosynthesis. The Journal of biological chemistry (1968), 243(8),1839-45.
Georgiadis M. M. et al. Crystallographic structure of the nitrogenase iron protein from *Azotobacter vinelandii*. Science (Washington, DC, United States) (1992), 257(5077), 1653-9.
Kim J., Rees D. C. Structural models for the metal centers in the nitrogenase molybdenum-iron protein. Science (Washington, DC, United States) (1992), 257(5077), 1677-82.
Einsle O., Tezcan F. A., Andrade S. L. A., Schmid B., Yoshida M., Howard J. B., Rees D. C. Nitrogenase MoFe-protein at 1.16 .ANG. resolution: A central ligand in the FeMo-cofactor. Science (Washington, DC, United States) (2002), 297(5587), 1696-1700.
Maragoudakis M. E., Strassman M. Homocitric acid accumulation by a lysine-requiring yeast mutant. Journal of Biological Chemistry (1966), 241(3), 695-9.
Li Z.-C., Xu J.-Q. An improved synthesis of homocitrate. Molecules [Electronic Publication] (1998), 3(2), 31-34.
Ancliff R. A., Russell A. T., Sanderson A. J. Resolution of a citric acid derivative: synthesis of (R)-(−)-homocitric acid-γ-lactone. Tetrahedron: Asymmetry (1997), 8(20), 3379-3382.
Thomas U., Kalyanpur M. G., Stevens, C. M. The absolute configuration of homocitric acid (2-hydroxy-1,2,4-butanetricarboxylic acid), an intermediate in lysine biosynthesis. Biochemistry (1966), 5(8), 2513-16.
Rodriguez G.H., Biellmann J.F. Enantioselective syntheses of (−)- and (+)-homocitric acid lactones. Journal of Organic Chemistry (Mar 8, 1996), 61(5), 1822-1824.
Ma G., Palmer D. R. J. Improved asymmetric syntheses of (R)-(−)-homocitrate and (2R,3S)-(−)-homoisocitrate, intermediates in the α-aminoadipate pathway of fungi. Tetrahedron Letters (2000), 41(48), 9209-9212.
Xu P.-F., Matsumoto T., Ohki Y., Tatsumi K. A facile method for synthesis of (R)-(−)- and (S)-(+)- homocitric acid lactones and related α-hydroxy dicarboxylic acids from D- or L-malic acid. Tetrahedron Letters (2005), 46(22), 3815-3818.
Paju A., Kanger T., Pehk T., Eek M., Lopp M. A short enantioselective synthesis of homocitric acid-γ-lactone and 4-hydroxy-homocitric acid-γ-lactones. Tetrahedron (2004), 60(41), 9081-9084.

* cited by examiner

*Primary Examiner* — Paul A Zucker
(74) *Attorney, Agent, or Firm* — Kristina M. Grasso, Esq. PLLC

(57) ABSTRACT

Archiral (2-hydroxy-3-oxo-cyclopent-1-enyl) acetic acid) alkyl, alkylphenyl and phenyl esters, and a simple and efficient method for the synthesis of both enantiomers of homocitric acid gamma-lactone and the corresponding salts from these esters are described. The method is based on asymmetric oxidation of esters, and the steps of basic and acidic hydrolysis and final acidic lactonization of the homocitric acid into homocitric acid gamma-lactone. The homocitric acid salts are obtained after basic treatment of homocitric acid gamma-lactone. The esters, conditions and reagents used in chemical conversion and separating products are important constituents affording efficient and simple method for production of homocitric acid gamma-lactone and homocitric acid salts.

14 Claims, 7 Drawing Sheets

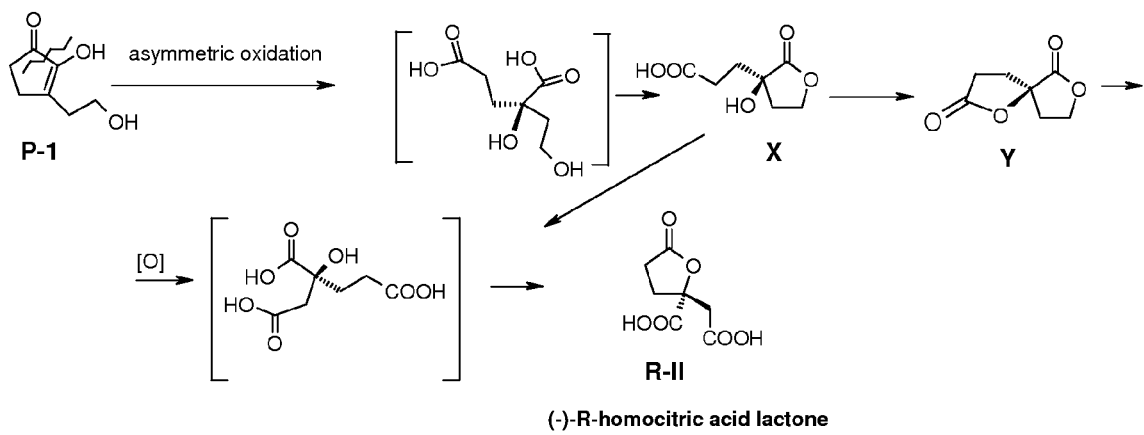
Figure 1: The reaction sequence for (-)-R-homocitric acid lactone

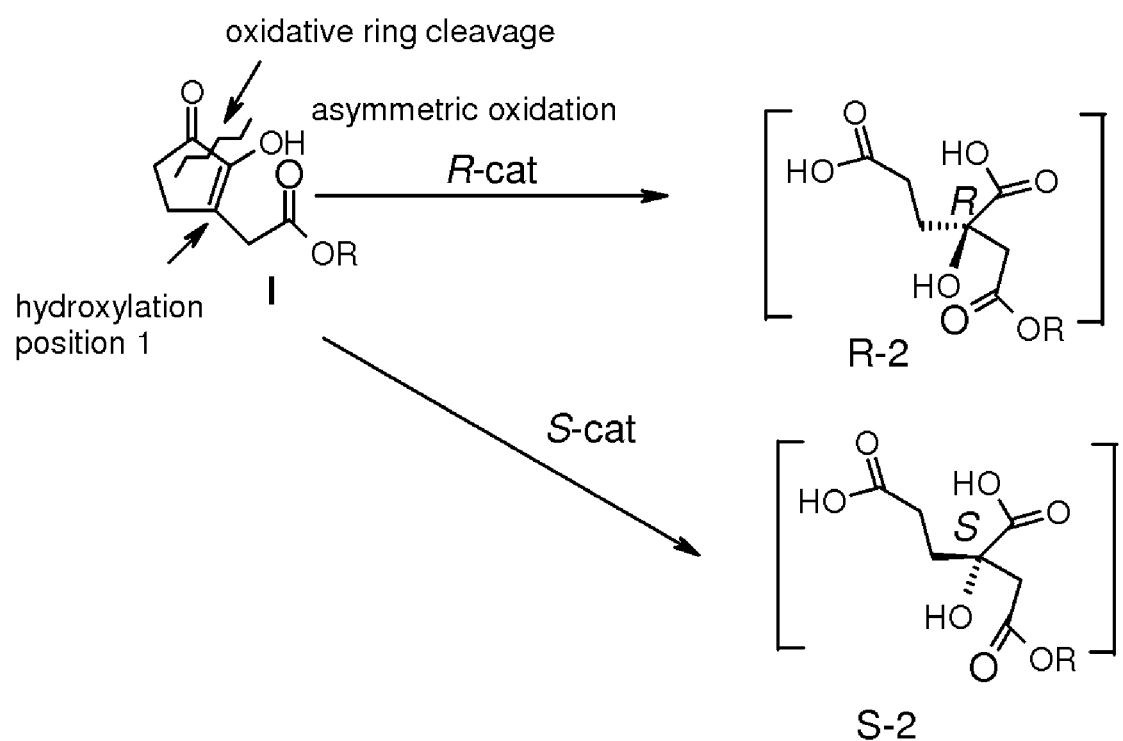
Figure 2: Stage A. Asymmetric oxidation.

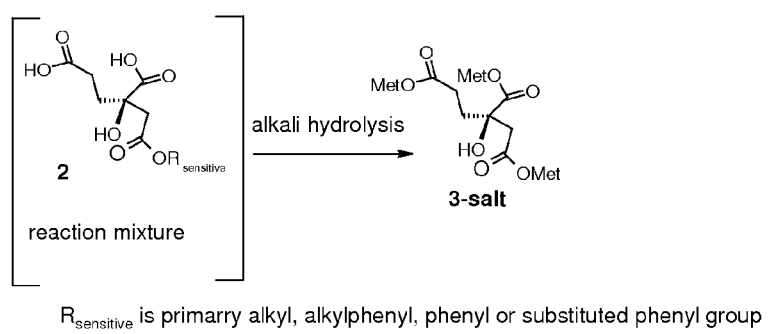
Figure 3: Stage B, Option 1. Hydrolysis of homocitric acid monoester 2 with alkali sensitive groups $R_{sensitive}$ to homocitric acid trisalt 3-salt.

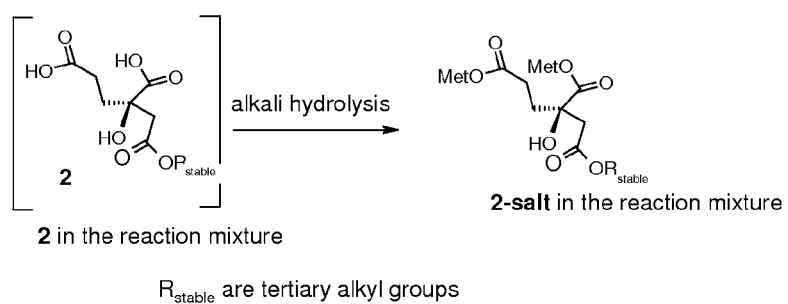
Figure 4: Stage B, Option 2. Hydrolysis of homocitric acid monoester 2 with alkali stable groups $R_{stable}$ to ester disalt *2-salt*

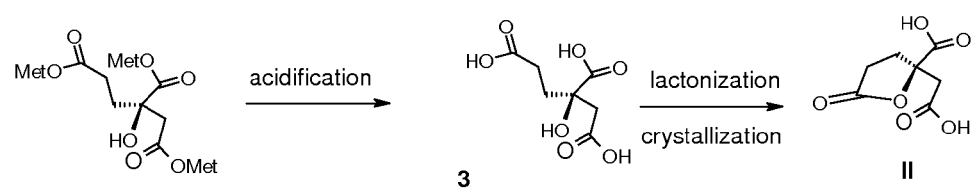
3-salt in the reaction mixture from Process B, Option 1
Figure 5: Stage C. Conversion of homocitric acid trisalt 3-salt from Stage B, Option 1 to homocitric acid γ-lactone II.

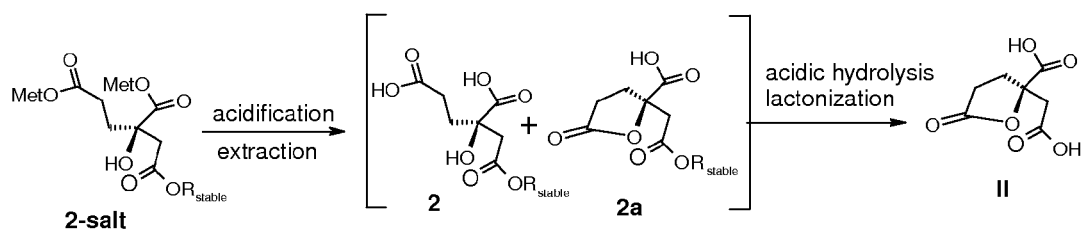
Figure 6: Stage C. Conversion of homocitric acid disalt 2-salt to homocitric acid lactone II.

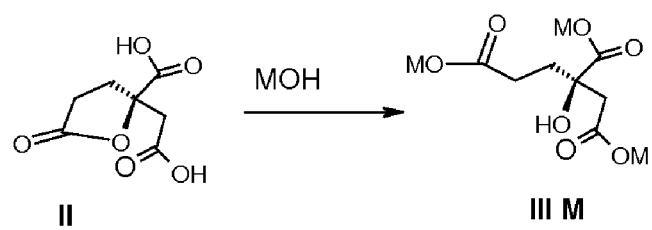
Figure 7: Conversion of homocitric acid II to homocitric acid trisalt III-M.

ESTERS OF (2-HYDROXY-3-OXO-CYCLOPENT-1-ENYL) ACETIC ACID AND THEIR USE FOR PREPARING (−)-R-HOMOCITRIC ACID GAMMA-LACTONE, (+)-S-HOMOCITRIC ACID GAMMA-LACTONE AND THE CORRESPONDING (−)-R-HOMOCITRIC ACID AND (+)-S-HOMOCITRIC ACID SALTS

TECHNICAL FIELD

The present invention relates to manufacturing of optically active hydroxy triacids, their salts and lactones: specifically to chemical asymmetric synthesis of both enantiomers of a natural hydroxy triacid lactone-homocitic acid lactone from a common achiral organic compounds esters of (2-hydroxy-3-oxo-cyclopent-1-enyl) acetic acid by the means of asymmetric chemical oxidation.

BACKGROUND ART (−)-R-Homocitric acid is an intermediate of biosynthesis of lysine in yeast and in some fungi. (−)-R-Homocitric acid is synthesized in these organisms in enzymatic condensation of α-ketoglutarate and acetylSCoA (Strassman, M.; Ceci, L. N. *Biochem. Biophys. Res. Commun.*, 1964, 14, 262. Strassman, M.; Ceci, L. N. *J. Biol. Chem*, 1965, 240, 4357. Hogg, R. W.; Broquist, H. P. *J. Biol. Chem*, 1968, 243, 1839). That pathway is absent in plants and mammalians. Because of that reason is (−)-R-homocitric acid a promising candidate for anti-fungi therapy in mammalians. Homocitric acid is also an important component of the FeMo-cofactor in nitrogenase, which is fixating air nitrogen (Georgiadis, M. M.; Komiya, H.; Chakrabarti, P.; Woo, D.; Kornuc, J. J.; Rees, D. *Science* 1992, 257, 1653. Kim, J.; Rees, D. C. *Science* 1992, 257, 1677. Einsle, O.; Tezcan, F. A.; Andrade, S. L. A.; Schmid, B.; Yoshida, M.; Howard, J. B; Rees, D. C. *Science* 2002, 297, 1696).

Racemic homocitric acid has been synthesized from hydrolysis of diethyl-α-ketoadipate cyanohydrin (Maragoudakis, M., Strassman, M. *J. Biol. Chem.*, 1966, 241, 695) and also starting from ethyl tert-butyl malonate in a three step procedure in 54% yield (Li, Z.-C.; Xu, J.-Q. *Molecules*, 1998, 3, 31).

The enantiomers of homocitric acid have been obtained by resolution of racemates that were obtained from the chemical synthesis. Thus, the R-enantiomer of homocitric acid γ-lactone has been also obtained by resolution of enantiomers from chemical synthesis in 10% overall yield (Ancliff, R. A., Rusell, T. A., J. Sanderson, A. J. *Tetrahedron: Asymmetry,* 1997, 8, 3379).

The enantiomers of homocitric acid were obtained by chemical synthesis starting from optically active natural compounds. Thus, S-homocitric acid was first obtained by means of chemical synthesis from (−)-quinic acid as an analytical sample (Thomas, U., Kalaynpur, M. G., Stevens, C. M. *Biochemistry,* 1966, 5, 2513). Also, S- and R-enantiomers of homocitric acid γ-lactones have been chemically synthesized starting from natural enantiomeric L-lactic acid and L-serine in a multistep procedure in low overall yield (Rodriguez, G. H., Bielmann J.-F. *J. Org. Chem.* 1996, 61, 1822).

The R-enantiomer of homocitric acid sodium salt was preparatively synthesized from D-malic acid Na-salt in 12% yield using a multiple step procedure (Ma, G.; Palmer, D. R. J. *Tetrahedron Lett.* 2000, 41, 9209). An improved synthesis of R-homocitric acid and S-homocitric acid from natural D- and L-malic acid correspondingly in a three step procedure in 32-33% overall yield was accomplished (Xu, P.-F.; Matsumoto, Y.; Ohki, Y.; Tatsumi, K. *Tetrahedron Letters,* 2005, 46, 3815. Xu, P.-F.; Tatsumi, K. Japan Patent Application, 2005, JP2005-075734).

An asymmetric synthesis procedure for R-homocitric acid and S-homocitric acid lactones starting from an achiral 3-hydroxyethyl cyclopentane-1,2-dione is described (Paju, A.; Kanger, T.; Pehk, T.; Eek, M.; Lopp, M. *Tetrahedron,* 2004, 60, 9081. Lopp, M.; Paju, A.; Pehk, T.; Eek, M.; Kanger, T. Estonian Patent Application EE200400009, decision to grant the patent issued). According to that procedure 3-hydroxyethyl cyclopentane-1,2-dione is transformed to the target compound using two subsequent oxidations (Scheme 1). Depending on the asymmetric oxidation catalyst both enantiomers of homocitric acid lactone—R-homocitric acid γ-lactone or S-homocitric acid lactone can be obtained. In the Scheme 1 the reaction sequence for the synthesis of R-homocitric acid lactone is presented.

From the first oxidation an optically active intermediate X (3-(3-hydroxy-2-oxotetrahydrofuran-3-yl)-propanoic acid R- or S-isomer is obtained in 75% yield. The method describes two options A and B. According to option A intermediate X is oxidized to the target compound II in 50 to 71% yield with $KMnO_4$ or with $K_2S_2O_8$ in the presence of $RuO_4$. According to option B intermediate X is transformed to 1,7-dioxaspiro[4.4]nonaan-2,6-diooniks (intermediate Y), which is subsequently oxidized to the target compound II. Both options require two different oxidation processes: asymmetric oxidation of 3-hydroxyethylcyclopentan-1,2-dione P-1 and then oxidation of the primary hydroxyl group which is in the scheme bound to the lactone moiety in the compounds X or Y. The described option B requires additionally the transformation of intermediate X to intermediate Y. These reasons make the described method for the synthesis of homocitric acid lactones inefficient.

BRIEF DESCRIPTION OF DRAWINGS

FIG. 1 is the reaction sequence for (−)-R-homocitric acid lactone.

FIG. 2 illustrates the asymmetric oxidation of the starting compound I.

FIG. 3 illustrates the hydrolysis of homocitric acid monoester 2 with alkali sensitive groups $R_{sensitive}$ to homocitric acid trisalt 3-salt.

FIG. 4 illustrates the hydrolysis of homocitric acid monoester 2 with alkali stable groups $R_{stable}$ to ester disalt 2-salt.

FIG. 5 illustrates the conversion of homocitric acid trisalt 3-salt from Stage B, Option 1 to homocitric acid γ-lactone II.

FIG. 6 illustrates the conversion of homocitric acid disalt 2-salt to homocitric acid lactone II.

FIG. 7 illustrates the conversion of homocitric acid II to homocitric acid trisalt III-M.

DISCLOSURE OF THE INVENTION

The object of the invention is a simple and efficient method for the synthesis of both enantiomers of homocitric acid γ-lactone II and the corresponding homocitric acid salts III. The object is achieved by novel process using new compounds, esters of (2-hydroxyl-3-oxo-cyclopent-1-enyl)-acetic acid (Compound I) as the starting compound for the synthesis of homocitric acid γ-lactone II and the corresponding homocitric acid salts III. The Compounds I are subjected to asymmetric oxidation resulting in one step to homocitric acid skeleton, which after hydrolysis and lactonization results in the homocitric acid γ-lactone II or, after basic hydrolysis homocitric acid trisalt III.

MODES FOR CARRYING OUT THE INVENTION

According to the present invention the starting compound is an ester of achiral (2-hydroxyl-3-oxo-cyclopent-1-enyl)-acetic acid I.

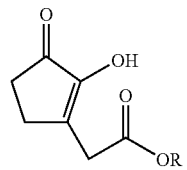

I where R is a alkali sensitive primary alkyl group $R_{sensitive}$ like $CH_3$, $C_2H_5$, etc; or primary alkylphenyl group like $—CH_2-Ph-X$, where X is H or any other substituent in the ring; or phenyl group like -Ph-X, where X is H or any other substituent in the ring
or
where R is alkali stable tertiary alkyl group $R_{stable}$ like $—C(CH_3)_3$, $—C(CH_3)_2C_2H_5$ etc.

According to the invention the transformation of the starting compound I to target homocitric acid γ-lactone II comprises the following three main stages: Stage A, asymmetric oxidation of starting compound I; Stage B, basic hydrolysis of the reaction mixture; Process C, separation of the target product and lactonization. To obtain homocitric acid salts γ-lactone II is hydrolyzed with alkali in separate process to afford homocitric acid trisalt III.

Stage A, asymmetric oxidation of the starting compound I means asymmetric hydroxylation of the ring at position 1 of an appropriate (2-hydroxyl-3-oxo-cyclopent-1-enyl)-acetic acid ester I, and oxidative ring cleavage of the cyclopentane ring between oxo- and enol hydroxyl group of the starting compound I. These two reactions together are considered as Stage A. That process transforms the starting compound I directly to the main skeleton of homocitric acid, and results in homocitric acid monoester 2. The R-enantiomer R-2 is obtained when R-cat is used as a catalyst in the Stage A, and the S-enantiomer S-2 is obtained when S-cat is used in Stage A. (Scheme 2)

According to the invention, the ester group R in Compound I is either alkali sensitive or alkali stable. In Stage A the ester group R in the compound I does not influence considerably the selectivity and the yield of the Stage A.

According the invention the enantiomeric catalyst R-cat for Stage A presents a mixture of $Ti(OiPr)_4$, (+)-diethyltartrate and tert-butyl hydroperoxide in a certain ratio of the components. The enantiomeric catalyst S-cat presents a mixture of $Ti(OiPr)_4$, (−)-diethyltartrate and tert-butyl hydroperoxide in a certain ratio of the components. In a preferred embodiment of the invention the ratio of $Ti(OiPr)_4$ and diethyltartrate in the asymmetric catalysts R-cat and S-cat is close to the ratio 1:1.6 (from 1:1 up to 1:2). It is important that the ratio of $Ti(OiPr)_4$ and the oxidant tBuOOH in R-cat and S-cat is close to 1:2 to 1:3.

In the asymmetric oxidation Stage A the efficiency is estimated according to the enantioselectivity of the Stage A which is measured by enantiomeric purity of the optically active compound and the yield of homocitric acid monoester 2. The enantiomeric purity is determined by enantiomeric excess of the compound 2 (presented as ee %), calculated according to the following formula ee %=(d−l)/d+l), where d means the quantity of (+) enantiomer and l means the quantity of (−) enantiomer. The selected compound to $Ti(OiPr)_4$ ratio is important as it enables to reach highest ee % value. According to the preferred embodiment of the invention the ratio of starting compound I and $Ti(OiPr)_4$ is close to 1:1.

Stage B comprises of basic hydrolysis of the reaction mixture after the asymmetric oxidation Stage A. Because of the hydrolysis conditions for alkali stable ester groups $R_{stable}$ and alkali sensitive ester groups $R_{sensitive}$ in ester 2 differ from each other, the hydrolysis conditions of compound 2 must be selected accordingly. Option 1 of the present invention means that alkali sensitive ester groups $R_{sensitive}$ selected from primary alkyl-, primary alkylaryl-, phenyl- and substituted phenyl groups, are used in the starting Compound I. The use of alkali sensitive alkyl groups $R_{sensitive}$ in compound I ultimately means that those groups exist also in intermediate 2. Option 2 of the present invention means that the alkali stable ester groups $R_{stable}$ selected from branched alkyl groups like $—C(CH_3)_3$, $—C(CH_3)_2C_2H_5$, $—C(CH_3)_2C_3H_7$ etc, are used in the starting compound I. The use of alkali stable alkyl groups $R_{stable}$ in compound I ultimately means that those groups exist also in intermediate 2.

According to Stage B Option 1, monoester 2 formed in Process I is hydrolyzed with alkali to the corresponding trisalt 3-salt (Scheme 3, Stage B, Option 1).

Also, all other ester groups present in the reaction mixture—tartaric acid ester, unreacted starting compound etc—hydrolyze to the corresponding salts.

According to Option 2 with alkali stable groups $R_{stable}$ in compound 2, homocitric acid monoester 2 formed in the oxidation step does not hydrolyze, and homocitric acid diasalt 2-salt is formed. (Scheme 4. Stage B, Option 2). All other ester groups present in the reaction mixture—tartaric acid ester, unreacted starting compound etc—hydrolyze to the corresponding salts.

Stage C, separation of the homocitric acid lactone II is different for trisalt 3-salt (product from Stage B, Option 1) and for ester disalt 2-salt (product from Stage B, Option 2). According to the invention conversion of 3-salt (the separation of the target product from Stage B, Option 1) is made by using acidification of the reaction mixture from Stage B, Option 1, resulting in the formation of homocitric acid 3. The obtained triacid 3 is converted to homocitric acid γ-lactone II by acidic lactonization with acid in a solvent. The type of acid is not essential. According to preferred embodiment of the invention the acid is HCl, acetic acid or trifluoroacetic acid in an organic solvent. After lactonization the target homocitric acid γ-lactone II is separated from the mixture by crystallization or chromatography (Scheme 5).

According to preferred embodiment of Stage C of the invention, conversion of 2-salt (from Stage B, Option 2) is made by using acidification of the reaction mixture from Stage B, Option 2, extraction of homocitric acid monoester 2 and partly lactonized ester lactone acid 2a, with an organic solvent. According to the preferred embodiment of the invention the organic solvent is ethyl acetate. The extracted mixture of 2 and 2a is converted to the target homocitric γ-lactone II, by acidic hydrolysis of 2 and 2a with a simultaneous lactonization of during hydrolyzation. The nature of acid is not essential. According to the preferred embodiment of the invention the hydrolysis and lactonization is performed with conc. HCl in organic solvent.

Homocitric acid γ-lactone II is converted to homocitric acid trisalt III by treatment with three equivalents of alkali (Scheme 7). The alkali converts the acid groups to salts and hydrolysis the lactone group to the acid salt resulting in a free tertiary hydroxyl group. According to the preferred embodiment of the invention the alkali is sodium, potassium or any other alkali.

EXAMPLES

Example 1

(Option 1) Synthesis of (−)-R-homocitric acid γ-lactone R-II starting from (2-hydroxy-3-oxo-cyclopent-1-enyl)-acetic acid ethyl ester Ia Used starting compound (2-hydroxy-3-oxo-cyclopent-1-enyl)-acetic acid ethyl ester Ia has the following physical parameters: $^1$H TMR (500 MHz, CDCl$_3$): δ 6.20 (bs, 1H, OH), 4.17 (q, J=7.3 Hz, 2H, OCH$_2$CH$_3$), 3.45 (s, 2H, CH$_2$CO), 2.55 (m, 2H, H-5), 2.45 (m, 2H, H-4), 1.26 (t, J=7.3 Hz, 3H, OCH$_2$CH$_3$); $^{13}$C TMR (125 MHz, CDCl$_3$): δ 203.25 (C-3), 169.60 (COO), 150.14 (C-2), 138.10 (C-1), 61.24 (OCH$_2$CH$_3$), 34.12 (CH$_2$CO), 32.00 (C-4), 25.28 (C-5), 14.04 (CH$_2$CH$_3$).

To a mixture of Ti(OiPr)$_4$ (0.44 ml; 1.47 mmol) in CH$_2$Cl$_2$ (9 ml, with 150 mg of a powder of 4 Å molecular sieves) under argon at −20° C. (+)-Diethyl tartrate (0.4 ml; 2.35 mmol) was added and the mixture was stirred for 15 minutes. After that starting diketone Ia (270 mg; 1.47 mmol) in CH$_2$Cl$_2$ (3 ml) was added and the mixture was stirred for 30 minutes. Now t-BuOOH (0.56 ml; 3.68 mmol, 6.6 M solution in decane) was added and the reaction mixture was kept at −20° C. for 64 hours.

To the reaction mixture water (9 ml) was added and the mixture was stirred at room temperature for 1 hour. Now 30% NaOH solution in NaCl (1.8 ml) at 0° C. was added and the mixture was stirred at room temperature for additional 1 hour. The reaction mixture was filtered, the CH$_2$Cl$_2$ layer was separated and the water phase was acidified with 1N HCl-ga (16 ml) until pH 1. Water was removed on rotatory evaporator, the residue was dissolved in acetone (80 ml) and filtered. The filtrate was concentrated in the rotatory evaporator treated with solution of 0.1 M HCl (100 ml). After removal of water and filtration of the precipitate, the filtrate was concentrated and purified on silica gel (Chemapol L40/100) using petrol ether:acetone 10:5-10:6 mixture). After evaporation of eluent 144 mg of the target compound (−)-(R)-homocitric acid γ-lactone R-II was obtained.

Example 2

(Option 1) Synthesis of (−)-R-homocitric acid γ-lactone R-II starting from (2-hydroxy-3-oxo-cyclopent-1-enyl) acetic acid methyl ester Ib Used starting compound (2-hydroxy-3-oxo-cyclopent-1-enyl)-acetic acid methyl ester Ib has the following physical parameters: $^1$H TMR (500 MHz, CDCl$_3$): δ 6.45 (bs, 1H, OH), 3.73 (s, 3H, OMe), 3.47 (s, 2H, CH$_2$CO), 2.56 (m, 2H, H-5), 2.46 (m, 2H, H-4); $^{13}$C TMR (125 MHz, CDCl$_3$): δ 202.83 (C-3), 169.96 (COO), 150.09 (C-2), 137.20 (C-1), 52.20 (OMe), 33.86 (CH$_2$CO), 31.97 (C-4), 25.29 (C-5). MS (EI): m/z (%)=170 (M$^+$, 47), 138 (100), 111 (59), 110 (52), 82 (57), 59 (25), 55 (72). IP ν=3314, 2961, 1730, 1700, 1656, 1438, 1391, 1270, 1224, 1114 cm$^{-1}$.

To a mixture of Ti(OiPr)$_4$ (0.30 ml; 1.0 mmol) in CH$_2$Cl$_2$ (6 ml, with 100 mg of a powder of 4 Å molecular sieves) under argon at −20° C. (+)-Diethyl tartrate (0.27 ml; 1.6 mmol) was added and the mixture was stirred for 15 minutes. After that starting diketone Ib (170 mg; 1.0 mmol) in CH$_2$Cl$_2$ (2 ml) was added and the mixture was stirred for 30 minutes. Now t-BuOOH (0.38 ml; 2.5 mmol, 6.6 M solution in decane) was added and the reaction mixture was kept at −20° C. for 64 hours.

To the reaction mixture water (6 ml) was added and the mixture was stirred at room temperature for 1 hour. Now 30% NaOH solution in NaCl (1.2 ml) at 0° C. was added and the mixture was stirred at room temperature for additional 1 hour. The reaction mixture was filtered, the CH$_2$Cl$_2$ layer was separated and the water phase was acidified with 1N HCl-ga (10 ml). Water was removed on a rotatory evaporator, the residue was dissolved in acetone (60 ml) and filtered. The filtrate was concentrated on a rotatory evaporator treated with solution of 0.1 M HCl (70 ml). After removal of water and filtration of the precipitate, the filtrate was concentrated and purified on silica gel (Chemapol L40/100) using petrol ether:acetone 10:5-10:6 mixture). After evaporation of the eluent 96 mg of the target compound (−)-(R)-homocitric acid γ-lactone R-II was obtained.

Example 3

(Option 1) Synthesis of (−)-R-homocitric acid γ-lactone R-II starting from (2-hydroxy-3-oxo-cyclopent-1-enyl) acetic acid phenyl ester Ic Used starting compound (2-hydroxy-3-oxo-cyclopent-1-enyl)-acetic acid phenyl ester Ic has the following physical parameters: $^1$H TMR (500 MHz, CDCl$_3$): δ 7.39 (dd, J=7.6 ja 8.1 Hz, 2H, meta), 7.25 (t, J=7.6 Hz, 1H, para), 7.12 (d, J=8.1 Hz, 2H, orto), 6.71 (s, 1H, OH), 3.72 (s, 2H, CH$_2$CO), 2.67 (m, 2H, H-5), 2.51 (m, 2H, H-4); $^{13}$C TMR (125 MHz, CDCl$_3$): δ 203.07 (C-3), 167.94 (COO), 150.43 (s), 150.36 (C-2), 137.03 (C-1), 129.42 (meta), 126.03 (para), 121.33 (orto), 34.06 (CH$_2$CO), 32.05 (C-4), 25.24 (C-5). MS (EI): m/z (%)=232 (M$^+$, 20), 139 (19), 138 (100), 111 (29), 94 (84), 82 (14), 77 (6), 65 (10), 55 (23). IP ν=3332, 1751, 1696, 1659, 1589, 1494, 1457, 1402, 1386, 1192, 1164, 1110 cm$^{-1}$ To a mixture of Ti(OiPr)$_4$ (0.48 ml; 1.6 mmol) in CH$_2$Cl$_2$ (10 ml, with 150 mg of a powder of 4 Å molecular sieves) under argon at −20° C. (+)-Diethyl tartrate (0.43 ml; 2.56 mmol) was added and the mixture was stirred for 15 minutes. After that starting diketone Ic (370 mg; 1.6 mmol) in CH$_2$Cl$_2$ (3 ml) was added and the mixture was stirred for 30 minutes. Now t-BuOOH (0.60 ml; 4.0 mmol, 6.6 M solution in decane) was added and the reaction mixture was kept at −20° C. for 65 hours.

To the reaction mixture water (10 ml) was added and the mixture was stirred at room temperature for 1 hour. Now 30% NaOH solution in NaCl (1.9 ml) at 0° C. was added and the mixture was stirred at room temperature for additional 1 hour. The reaction mixture was filtered, the CH$_2$Cl$_2$ layer was separated and the water phase was acidified with 1N HCl-ga (12 ml). Water was removed on a rotatory evaporator, the residue was dissolved in acetone (80 ml) and filtered. The filtrate was concentrated on a rotatory evaporator treated with solution of 0.1 M HCl (twice with 50 ml). After removal of water and filtration of the precipitate, the filtrate was concentrated and purified on silica gel (Chemapol L40/100) using petrol ether:acetone 10:5-10:6 mixture). After evaporation of the eluent 163 mg of the target compound (−)-(R)-homocitric acid γ-lactone R-II was obtained.

Example 4

(Option 2) Synthesis of (−)-R-homocitric acid γ-lactone R-II starting from (2-hydroxy-3-oxo-cyclopent-1-enyl) acetic acid tert-butyl ester Id Used starting compound (2-hydroxy-3-oxo-cyclopent-1-enyl)-acetic acid tert-butyl ester Id has the following physical parameters: $^1$H TMR (500 MHz, CDCl$_3$): δ 6.78 (s, 1H, OH), 3.36 (s, 2H, CH$_2$CO), 2.53 (m, 2H, H-5), 2.42 (m, 2H, H-4), 1.44 (s, 9H, tert-Bu); $^{13}$C TMR (125 MHz, CDCl$_3$): δ 203.08 (C-3), 168.86 (COO), 150.04 (C-2), 138.50 (C-1), 81.71 (OC(Me)$_3$), 35.48 (CH$_2$CO), 32.01 (C-4), 27.95 (OC(Me)$_3$), 25.30 (C-5). MS (EI): m/z=212 (M$^+$), 156, 139, 111, 82, 57. IP ν=3307, 2999, 2973, 1728, 1699, 1665, 1415, 1384, 1366, 1151 cm$^{-1}$. MS (EI): m/z=212 (M$^+$), 156, 139, 111, 82, 57, 41, 29. IP ν=3307, 2999, 2973, 1728, 1699, 1665, 1415, 1384, 1366, 1151, 699 cm$^{-1}$.

To a mixture of Ti(OiPr)$_4$ (0.30 ml; 1.0 mmol) in CH$_2$Cl$_2$ (6 ml, with 100 mg of a powder of 4 Å molecular sieves) under argon at −20° C. (+)-Diethyl tartrate (0.27 ml; 1.6 mmol) was added and the mixture was stirred for 15 minutes. After that starting diketone Id (212 mg; 1.0 mmol) in CH$_2$Cl$_2$ (2 ml) was added and the mixture was stirred for 30 minutes. Now t-BuOOH (0.38 ml; 2.5 mmol, 6.6 M solution in decane) was added and the reaction mixture was kept at −20° C. for 63 hours.

To the reaction mixture water (6 ml) was added and the mixture was stirred at room temperature for 1 hour. Now 30% NaOH solution in NaCl (1.2 ml) at 0° C. was added and the mixture was stirred at room temperature for additional 1 hour. The reaction mixture was filtered, the CH$_2$Cl$_2$ layer was separated and the water phase was acidified with 1N HCl-ga (9 ml). Separated water phase was extracted with EtOAc (6 times with 20 ml), organic layer was dried on MgSO$_4$ and concentrated in vacuum. The obtained crude product was dissolved in CH$_2$Cl$_2$ (40 ml) and conc. HCl (0.4 ml) was added. The mixture was stirred at room temperature for 2 hours, concentrated in vacuum and treated with EtOAc:toluene (2:1). The product was purified on silica gel (Chemapol L40/100) using petrol ether:acetone 10:5-10:6 mixture). After evaporation of the eluent 100 mg of the target compound (−)-(R)-homocitric acid γ-lactone R-II was obtained.

Example 5

(Option 2) Synthesis of (−)-R-homocitric acid γ-lactone R-II starting from (2-hydroxy-3-oxo-cyclopent-1-enyl) acetic acid tert-amyl ester Ie Used starting compound (2-hydroxy-3-oxo-cyclopent-1-enyl)-acetic acid tert-amyl ester Ie has the following physical parameters: $^1$H TMR (500 MHz, CDCl$_3$): δ 6.85 (s, 1H, OH), 3.38 (s, 2H, CH$_2$CO), 2.53 (m, 2H, H-5), 2.43 (m, 2H, H-4), 1.75 (q, J=7.3 Hz, 2H, CH$_2$CH$_3$), 1.42 (s, 6H, (CH$_3$)$_2$), 0.86 (t, J=7.3 Hz, 3H, CH$_2$CH$_3$); $^{13}$C TMR (125 MHz, CDCl$_3$): δ 203.16 (C-3), 168.80 (COO), 150.04 (C-2), 138.61 (C-1), 84.24 (OC(Me)$_2$), 35.42 (CH$_2$CO), 33.36 (CH$_2$CH$_3$), 32.01 (C-4), 25.36 (OC(Me)$_2$ ja C-5), 8.09 (CH$_3$CH$_2$). MS (EI): m/z (%)=226 (M$^+$), 156 (24), 139 (23), 111 (20), 71 (66), 55 (19), 43 (100). IP ν=3315, 2979, 2937, 2885, 1727, 1699, 1665, 1465, 1386, 1193, 1149 cm$^{-1}$. MS (EI): m/z (%)=226 (M$^+$), 156 (24), 139 (23), 111 (20), 71 (66), 55 (19), 43 (100), 41 (12), 39 (10). IP ν=3315, 2979, 2937, 2885, 1727, 1699, 1665, 1465, 1386, 1193, 1149 cm$^{-1}$.

To a mixture of Ti(OiPr)$_4$ (0.32 ml; 1.05 mmol) in CH$_2$Cl$_2$ (6 ml, with 100 mg of a powder of 4 Å molecular sieves) under argon at −20° C. (+)-Diethyl tartrate (0.28 ml; 1.68 mmol) was added and the mixture was stirred for 15 minutes. After that starting diketone Ie (237 mg; 1.05 mmol) in CH$_2$Cl$_2$ (2 ml) was added and the mixture was stirred for 30 minutes. Now t-BuOOH (0.40 ml; 2.63 mmol, 6.6 M solution in decane) was added and the reaction mixture was kept at −20° C. for 66 hours.

To the reaction mixture water (6 ml) was added and the mixture was stirred at room temperature for 1 hour. Now 30% NaOH solution in NaCl (1.2 ml) at 0° C. was added and the mixture was stirred at room temperature for additional 1 hour. The CH$_2$Cl$_2$ layer was separated and the water phase was acidified with 1N HCl-ga (10 ml). Separated water phase was extracted with EtOAc (2 times with 30 ml and 1 time with 20 ml), organic fractions were joined and dried on MgSO$_4$ and concentrated in vacuum. The obtained crude product was dissolved in CH$_2$Cl$_2$ (40 ml) and conc. HCl (0.4 ml) was added. The mixture was stirred at room temperature for 3 hours, concentrated in vacuum and treated with EtOAc:toluene (2:1). The product was purified on silica gel (Chemapol L40/100) using petrol ether:acetone 10:5-10:6 mixture). After evaporation of the eluent 123 mg of the target compound (−)-(R)-homocitric acid γ-lactone R-II was obtained.

Example 6

Synthesis of (−)-R-homocitric Acid Sodium Salt R-III Na

To a solution of (−)-(R)-homocitric acid lactone R-II (49 mg, 0.26 mmol) in bidistilled water (2 ml) NaOH (0.76 ml, 0.78 mmol) was added and the mixture was stirred at room temperature for 1.5 hours. The reaction mixture was concentrated in vacuum to afford 78 mg of (−)-R-homocitric acid sodium salt R-III Na as a white solid.

The exemplary embodiments presented herein illustrate the principles of the invention and are not intended to be exhaustive or to limit the invention to the form disclosed; it is intended that the scope of the invention be defined by the claims appended hereto and their equivalents.

The invention claimed is:

1. Esters of (2-hydroxy-3-oxo-cyclopent-1-enyl) acetic acid of formula I

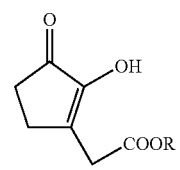

where R designates an alkyl group or a phenyl group.

2. The esters according to claim 1, wherein R is a primary alkyl group, a primary alkylphenyl group or a phenyl group, and wherein said esters are alkali sensitive.

3. The esters according to claim 1, wherein R is a tertiary butyl group or a tertiary amyl group, and wherein said esters are alkali stable.

4. The esters according to claim 1, wherein said esters are used for preparation of (−)-R-homocitric acid gamma-lactone.

5. The esters according to claim 1, wherein said esters are used for preparation of (+)-S-homocitric acid gamma-lactone.

6. A method for preparation of enantiomers of homocitric acid gamma-lactone comprising the step of asymmetric oxidation of esters of (2-hydroxy-3-oxo-cyclopent-1-enyl)acetic acid of formula I,

I wherein R designates an alkyl group or a phenyl group, with Ti(OiPr)$_4$, (+)-R,R-tartaric acid ester or (−)-S,S-tartaric acid ester, and tBuOOH.

7. The method of claim 6, wherein the ratio of Ti(OiPr)$_4$ and tBuOOH is from 1:2 to 1:3.

8. The method of claim 6, wherein the ratio of Ti(OiPr)$_4$, (+)-R,R-tartaric acid ester is from 1:1 to 1:3.

9. The method of claim 6, wherein the ratio of Ti(OiPr)$_4$, (−)-S,S-tartaric acid ester is from 1:1 to 1:3.

10. The method of claim 6, wherein the ratio of said ester and Ti(OiPr)$_4$ is 1:0.1 to 1:1.

11. A method for preparation of (−)-R— and (+)-S-homocitric acid salts

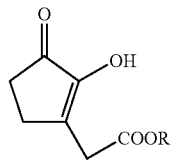

I comprising the steps of:
preparing homocitric acid gamma-lactones using esters of (2-hydroxy-3-oxo-cyclopent-1-enyl)acetic acid of formula I wherein R designates an alkyl group or a phenyl group;
treating said gamma-lactones correspondingly with three equivalent of the appropriate alkali; and
separating the formed salts.

12. Ester of (2-hydroxy-3-oxo-cyclopent-1-enyl)acetic acid of formula I

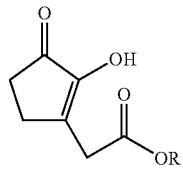

I wherein R designates a tertiary alkyl group, and wherein the tertiary alkyl group is —C(CH$_3$)$_3$, —C(CH$_3$)$_2$C$_2$H$_5$.

13. Ester of (2-hydroxy-3-oxo-cyclopent-1-enyl)acetic acid of formula I wherein R designates a primary alkyl group, wherein the primary alkyl group is CH$_3$,

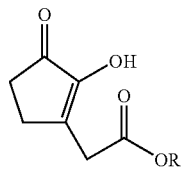

I

C$_2$H$_5$, a primary alkylphenyl group, wherein the primary alkylphenyl group is —CH$_2$-Ph-X, or a phenyl group, wherein the phenyl group is -Ph-X, wherein X is H or any other substituent in the ring.

14. The method of claim 6, comprising alkali treatment of asymmetric oxidation reaction mixture, acidification, extraction with organic solvent and lactonization.

* * * * *